United States Patent [19]

Hawes

[11] 4,054,384
[45] Oct. 18, 1977

[54] SAMPLE-BACKGROUND-SIGNAL AUTOCANCELLATION IN FLUID-SAMPLE ANALYZERS, USING SYMMETRICAL TIME-DELAY OR TIME-AVERAGING

[76] Inventor: Roland C. Hawes, 771 Oakglade Drive, Monrovia, Calif. 91016

[21] Appl. No.: 743,155

[22] Filed: Nov. 18, 1976

Related U.S. Application Data

[63] Continuation of Ser. No. 574,618, May 5, 1975, which is a continuation-in-part of Ser. No. 416,233, Nov. 15, 1973, Pat. No. 3,897,154.

[51] Int. Cl.² .......................... G01N 21/34; G01J 3/42
[52] U.S. Cl. ....................................... 356/51; 73/23.1; 250/345; 356/106 S; 356/181; 356/205
[58] Field of Search .................... 356/51, 88, 89, 93, 356/94, 95, 106 S, 181, 205, 206; 250/345, 575; 73/23.1

[56] References Cited

U.S. PATENT DOCUMENTS 3,345,859 10/1967 Fenske ................................ 73/23.1
3,992,109 11/1976 Bock .................................. 356/181

Primary Examiner—Vincent P. McGraw
Attorney, Agent, or Firm—Peter I. Lippman

[57] ABSTRACT

Apparatus and process provide qualitative and quantitative analysis of sample constituent(s) in a stream of fluid, relatively free from qualitative ambiguities and quantitative zero displacements due to slowly changing contamination in the measurement stream. Slowly changing zero displacement of a continuous measurement signal — caused by slowly changing contaminant concentrations in the stream — is cancelled out by deriving two continuous versions of the measurement signal, both being time-distorted, and continuously manipulating the two versions as by subtraction.

One of the two time-distorted versions serves as a primary or "main" signal; this main signal version is distorted in such a way that the time distortion of the other signal version is roughly symmetrical with respect to the main signal version, to improve measurement accuracy when the rate of zero displacement is nonlinear. In the case of spectral analysis, particular advantages lie in removal of misleading "background" spectral components.

13 Claims, 13 Drawing Figures

SAMPLE-BACKGROUND-SIGNAL AUTOCANCELLATION IN FLUID-SAMPLE ANALYZERS, USING SYMMETRICAL TIME-DELAY OR TIME-AVERAGING

CROSS-REFERENCES TO RELATED APPLICATIONS

This is a continuation of my copending application Ser. No. 574,618, for "Sample-Background-Signal Autocancellation in Fluid-Sample Analyzers," filed May 5, 1975; which was in turn a continuation-in-part of my then-copending application Ser. No. 416,233, for "Sample-Background Autocancellation in Fluid-Sample Analyzers," filed Nov. 15, 1973 and issued July 29, 1975 as U.S. Pat. No. 3,897,154.

BACKGROUND OF THE INVENTION

This invention relates to the problem of determining unknown constituents and/or measuring constituent concentrations in a fluid, under circumstances such that a "contaminant" or extraneous constituent of the fluid interferes with monitoring of the constituent sought. If the contaminant concentration fluctuates, accurate subtraction of the background due to the contaminant is difficult. Resort to dual-channel monitoring systems (that is, addition of a "reference" monitor) can solve the problem only if it is possible to provide a second fluid stream which contains substantially just the contaminant — and the contaminant therein must be at concentrations which accurately track the contaminant concentrations in the sample fluid.

A case in point is the analysis of a gas sample by gas chromatography. Such measurements can be particularly valuable when using an infrared spectrometer as a detector, because qualitative as well as quantitative analysis is possible. In such instrumentation, one of the significant limitations upon measurement accuracy is error due to contamination of the sample by gaseous material which "bleeds" from the coating on the adsorbing surface in the chromatographic column. Such bleeding of the column coating material is especially troublesome in "temperature-programmed" gas chromatography, wherein the rising column temperature tends to volatilize or decompose the adsorbing material, yielding constituents in the effluent which are unrelated to the test sample being analyzed. In such a case it is not obvious how to obtain a signal related purely to the bled coating material; consequently it has in prior devices not been possible to obtain saisfactory correction for or cancellation of the bled coating.

Some workers have attempted to solve this problem by providing a second chromatographic column, not injected with the sample gas, to provide suitable background gas for the reference cell of the spectrometer. This technique requires that the two columns be closely matched as to the coated adsorbing layer, on either the column wall or its packing, and as to carrier-gas flow rate as well as temperature, throughout their respective lengths. An accurate balance is not easily maintained.

Similar difficulties can arise in the case of a chromatograph operated with a carrier gas which has a constituent (such as, for example, either a contaminant, or the carrier gas itself) which interferes with measurement of the sample gas.

Analogous unsatisfactory background-matching attempts are familiar in other fluid-stream-measurement situations.

In measurements employing spectrally-distinguished characteristics, regardless of whether chromatographs are used, it is possible for the spectral effect of an extraneous constituent of even very weak concentration to interfere with interpretation of the spectrum of a desired constituent — because the extraneous constituent may have relatively intense spectral features.

My invention resolves all these difficulties for situations in which the contaminant concentration in a fluid stream changes slowly compared with the sample-constituent concentration(s) of interest.

My aforementioned U.S. Pat. No. 3,897,154 describes one solution to the problem described above, which solution involves directing the fluid stream through both measuring stations of a dual-channel monitoring system. The following ten paragraphs are devoted to describing the general concept of my invention as described in my aforementioned patent. It should be emphasized that these paragraphs are for reference only and do not describe the specific aspects of my invention to which the claims of this application are addressed.

SUMMARY OF PARENT APPLICATION

As pointed out in that patent, it is advantageous (though not strictly necessary) that the stream pass through both stations in series, placing the slowly-changing contaminant material in both stations at once, at very nearly the same concentrations, so as to permit an accurate balancing-out of the interference due to the contaminant. Sample constituent concentrations in the stream change more rapidly, so each sample constituent can be substantially all in one station at a time — first substantially all in a particular one of the two stations, then substantially all in the other station.

Thus in gas chromatography using a dual-beam infrared spectrometer (particularly a dual-input interferometric spectrometer) as a detector, the effluent gas from the chromatographic column passes through both the spectrometer "sample" and "reference" cells — advantageously, but not necessarily, in series. The spectrometer measurement light beams thus respectively pass through very nearly equal concentrations of bleed from the chromatographic column (or interfering carrier-gas constituent, as the case may be). In some such systems the conventional distinction between sample and reference paths disappears; while in other such systems this distinction is maintained.

In the first form of the invention, which may be called the "flow-delay" form, the flow path is such as to effect a time delay between arrival of each sample constituent at the two stations respectively — a delay which is substantial compared with the effective residence time of the stream in (at least) the station at which the sample arrives first. The two signals from the respective measurement stations may, in general, be compared with each other and interpreted in various ways including but not limited to subtraction of one signal from the other.

Other mathematical functions of the two signals may provide contaminant-effect autocancellation, and may very well be equally or even more advantageous, and are within the scope of my invention; but I have preferred to explore the subtractive function.

In the subtractive approach, the output signal undergoes an excursion first in one direction and then in the other — the two measurement stations alternately assuming the roles of sample and reference as the sample constituent arrives in first one station and then the other. This bidirectional signal pattern may be simply displayed for human interpretation on an analog or digital meter or (preferably) recorder: a skilled person can associate each such signal pattern with a sample constituent passing through the system at a particular time, and thereby determine the concentration of that constituent at that time.

However, I consider it preferable first to apply some additional data processing, because (1) the bidirectional signal patterns are an unconventional representation, an artifact of the measurement process; as such they require an additional level of understanding on the part of the human interpreter; and (2) the system response in one direction due to passage of one constituent of the sample through one measurement station may happen to occur at substantially the same time as a response in the opposite direction due to passage of a different constituent of the sample through the other measurement station — thereby distorting the bidirectional signal patterns for both constituents. This second reason can be particularly important if both excursions of a particular constituent's bidirectional signal pattern happen to be subject to such distortion, leaving no simply interpretable signal level as representative of the concentration of that constituent (though in fact a sophisticated interpretation scheme can disclose the information present with as much certainty as in more-usual representations).

A particularly effective kind of data processing, applicable to the simple-subtraction comparison method mentioned already, is integration of the bidirectional signal. This, as will be shown, minimizes the effects of interconstituent signal cancellation, and permits a unidirectional signal pattern. If suitable delay between sample arrival at the two measurement stations can be provided, the integration technique also makes the signal-excursion "shape" very simple, and thus amenable to ready interpretation by semiskilled personnel.

In a second form of the invention, which may be called the "dilution" form, the sample stream before passage into one of the two measurement stations passes first into a relatively large dilution chamber. This chamber may entirely precede the station concerned, along the flow path (so that in series-flow systems it is entirely along the flow path between the two measurement stations), or it may include the station itself (in series-flow systems, the second measurement station along the flow stream). In either case, if the dilution chamber is sufficiently large relative to the volume of each sample constituent, the sample-constituent concentration in the measurement station which is associated with the dilution chamber may be neglected.

The dilution form of the invention is amenable to simpler interpretive procedures, since the measurement station which contains the diluted sample constituents serves straightforwardly as a reference channel; however, the dilution form of the invention is limited to instances in which the contaminant concentrations change quite slowly relative to the effective residence time in the dilution chamber. In such instances the dilution form of the invention is preferred for its resultant interpretive simplicity. In many situations, however, the requirement that contaminant concentrations change slowly is unacceptable; for example, in many programmed-temperature gas chromatographs, the bleed concentration can change significantly in much less than a minute. In such instances the flow-delay form of the invention is preferred for its relatively rapid accommodation to changing contaminant levels.

In practice the two effects which produce these two forms of the invention are almost never completely separable: there is always some mixing or dilution of sample constituents (and resultant broadening of constituent "peaks") even in passage of the sample fluid through the measurement stations; and there is almost always some effective delay in passage of the greatest concentration of a given constituent from the center of one measurement station to the center of the other, even if the flow path between stations is a short conduit. (One exception is in the case of a parallel-flow arrangement of the dilution form of my invention.)

GENERAL CONCEPT OF THE INVENTION

All of the foregoing discussion reflects concepts appearing in my aforementioned patent. The present application is directed to an extension of those concepts, whereby the same and even additional advantages may be obtained without the necessity of providing duel sampling and measurement stations.

In the present invention, only one measurement station is provided, and only one continuous measurement signal is generated thereby. However, in a manner analogous to the prior generation of two measurement signals from a single fluid stream, my present invention forms two "versions" of the single continuous measurement signal — both formed in response to the said single continuous signal. At least one of these signal versions undergoes a time distortion relative to the single continuous signal, and relative to the other version. The time distortion may take the form of a signal delay (analogous to the flow delay form of my invention) or a signal averaging over a time period (analogous to the "dilution" form of my invention) — or in some advantageous cases both delay and averaging may be employed in one or the other derived version of the single continuous signal.

In any case the two versions of the single signal may be manipulated in very much the same ways as the two separate signals of my aforementioned patent — by using subtraction of one version from another, or possibly other mathematical functions of the two versions, having the effect of mutual cancellation of the signal component(s) due to slowly-changing background impurities of whatever origin. The present forms of my invention have some advantages relative to the forms of my invention disclosed and claimed in my aforementioned patent:

1. In the flow delay form of my invention, taking readings from the peaks of measurement signals, there can sometimes be a very small measurement error due to unavoidable dilution of the sample in the fluid stream, while the sample is passing between the two measurement stations: the sample "slug" diffuses both forward and backward along the flow path, at the same time as it is carried forward in the fluid stream; this tends to make the resulting "negative-going" measurement-signal peaks from the second measurement station shallower and wider than the positive peaks from the first station. If a later positive peak happens to be superposed upon the negative-going peak from a previously-arriving sample constituent, the arithmetic correction applied to that later peak to remove the effects of the earlier constituent would be based on the height of the positive-going peak for the earlier constituent and thus would be too large a correction; consequently the later-arriving constituent could inadvertently be assigned a concentration very slightly smaller than its true concentration. (This small error would not be present if integration of the bidirectional signal is employed as previously mentioned.)

Such error is eliminated in the "signal-delay" form of my invention, since the signal waveshape can be preserved during the delay, to virtually any specified degree of accuracy.

2. Also in the signal-delay form, since the delay is provided by electronic or other artificial storage means ("artificial" in the sense that the sample fluid flow is not itself being delayed or rerouted), the duration of the delay may be made easily adjustable — for greatest adaptability to various kinds of samples, in facilitating intepretation of the signal — and particularly in making the resulting difference (or other comparison) signal amenable to the integration technique.

3. Also in the signal-delay form, by comparing the main signal version with an arithmetic mean of two other versions, one delayed and one in effect advanced, the comparison may in effect be taken with a zero mean delay for purposes of background-signal fluctuation but a nonzero delay for purposes of obtaining a measure of the background which is not confused with a peak. This eliminates error due to linear monotonic drift of the background signal. To obtain this advantage the main signal is delayed as well as one to be found (namely, the version which is nominally delayed), but the main signal is not delayed as much as the nominally delayed signal version. This improvement may in principle also be obtained in the flow-delay form of my invention by providing a third series measurement station, and using the mean of the signals from the first and third stations for subtraction from the signal from the second station; however, this may not be practical.

4. In the "signal-averaging" form, by applying delay to one version as well as time-averaging the other, the time-averaging may in effect be taken over a time period which is centered about the instant of the unaveraged version. This minimizes error due to even nonlinear monotonic drift of the background signal. This improvement may in principle also be obtained in the dilution form of my invention by delaying the measurement signal from the station containing the undiluted sample; however, the very lengthy delays required, and the diffusion which the sample slug undergoes during the delay, tend to make this impractical.

5. Since general-purpose computation equipment is generally necessary in any sophisticated system for interpreting fluid-stream measurements — and this is particularly true for chromatographic and/or interferometric measurements — the requirement for storage or averaging is not in most cases apt to increase system cost significantly — while the sampling hardward simplifications may often represent significant cost reductions.

6. In both the flow-delay and dilution systems, very small imperfections in autocancellation of the background, an in determining corrections when positive- and negative-going signals are superposed (as discussed under (1), above), may result from imperfections in matching of the two measurement stations. For example, in optical systems the condition of the cell windows may vary; and in systems employing separate measurement detectors for the two stations the detector responses may not track accurately even during a measurement run.

In the signal-delay and signal-averaging forms of my invention, all station-matching errors are eliminated.

Numerous prior-art systems record background signals — particularly spectral information — for comparison with mixed sample-and-background signals to extract sample information from the latter. My invention is distinguished from such prior-art devices as follows: (1) it is not necessary in my invention to know what contaminants are present and to select appropriate spectra for such contaminants, to be subtracted from the mixed signal; whatever the contaminants are, their effects are autocancelled; and (2) it is not necessary in my invention to adjust the amplitude of the contaminant signal to "zero out" a particular contaminant peak or the like; all background contaminant signals accurately autocancel.

The various details and advantages of my present invention claimed herein may be more fully understood by reference to the accompanying drawings, of which:

DETAILED DISCUSSION

Figure 1:
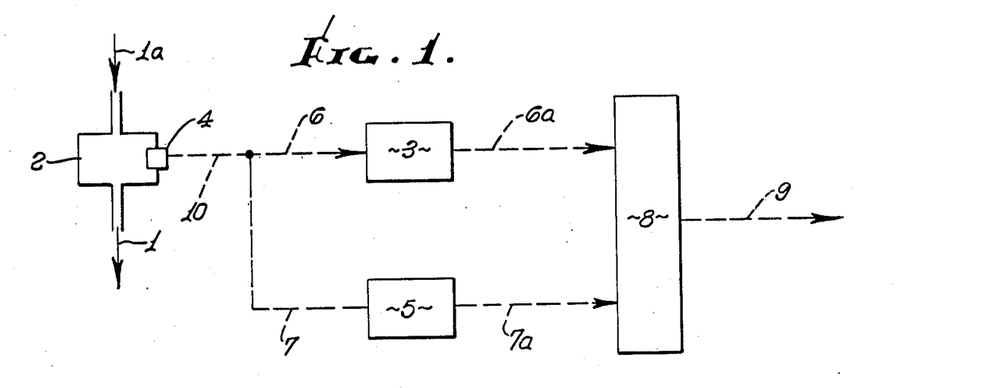
FIG. 1 is a schematic representation of the flow pattern and signal path for my present invention.

FIG. 1 illustrates the general concept of my invention. In this figure, 1a is a fluid stream entering a monitoring system, and 1 is the same fluid stream leaving the monitoring system. Within the monitoring system the fluid stream traverses only a single monitoring station 2. Associated with monitoring station 2 is sensing means 4 which imparts to the monitoring station the capability of deriving signal 10 in response to the presence of one or more sample constituents in the fluid stream. This signal is directed at 6 and 7 to time-distortion modules 3 and 5 respectively, wherein delay and/or time-averaging of the respective signals may occur.

The delayed and/or time-averaged and/or unchanged (depending upon the form of the invention which is in use) signals proceed at 6a and 7a to processor 8 which in effect derives a difference (or other mathematical combination) signal — and which may also integrate or otherwise process the difference (or other) signal — for display, storage, or other functional connection as an output signal 9.

In process-control systems or the like, the output signal 9 may be utilized to operate a control component such as a switch, valve, or more complex control element, to effect functional control of a production process, or a safety system, or other apparatus. All such devices — whether display, storage, control, and/or other signal-utilizing devices — for using the output signal 9 are referred to herein as "utilization means," while for simplicity only one type of utilization means is illustrated in the moredetailed drawings.

Because signal components arising from slowly-changing contaminant materials in station 2 are present with substantially identical amplitudes at inputs 6 and 7 to the time-distortion units 3 and 5, their effects substantially cancel out in the output signal 9 for subtractive processors 8. In this disclosure only subtractive processing, and subsequent integration of the resulting difference signal, will be discussed in detail — though my invention is not limited thereto, and other mathematical functions may be used without necessarily departing from the scope of the invention.

Figure 2:
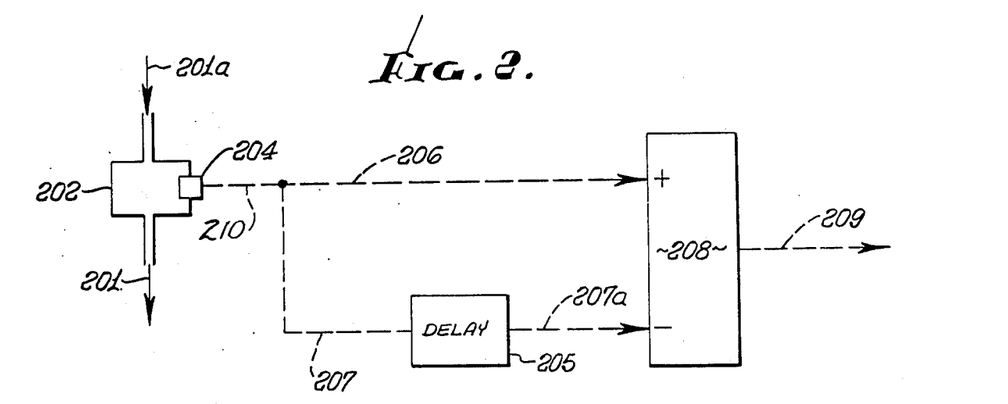
FIG. 2 is a schematic representation showing the signal path for the signal-delay form of my invention.

In FIG. 2, fluid enters and leaves the measurement system at 201a and 201, respectively, traversing as before measurement station 202 which has sensing means 204. These sensing means in cooperation with the measurement station derive signal 210, which is presented at 206 directly to one input terminal of processor 208; and presented at 207 too to the input of delay device 205, whose delayed output at 207a enters the other input terminal of processor 208. The two inputs at 206 and 207a are processed at 208 to produce an output signal directed at 209 to utilization means. Here however the generalized time-distortion unit 5 of FIG. 1 is explicitly a delay device 205, and the analogous unit 3 introduces no distortion and consequently is represented as an uninterrupted signal line. As to selection of suitable delay time to be effected at 205, it will be clear that if the quantity and concentration of a particular sample constituent are such that nearly all of the measurement signal resulting from the constituent being within measurement station 202 occurs during a time interval shorter than the delay time introduced at 205, then the signal component at 207a resulting from that same constituent will typically be negligible, during that same time interval. As will be seen later, it is not necessary to provide such a long delay to practice successfully the signal-delay form of my invention.

Figure 6:
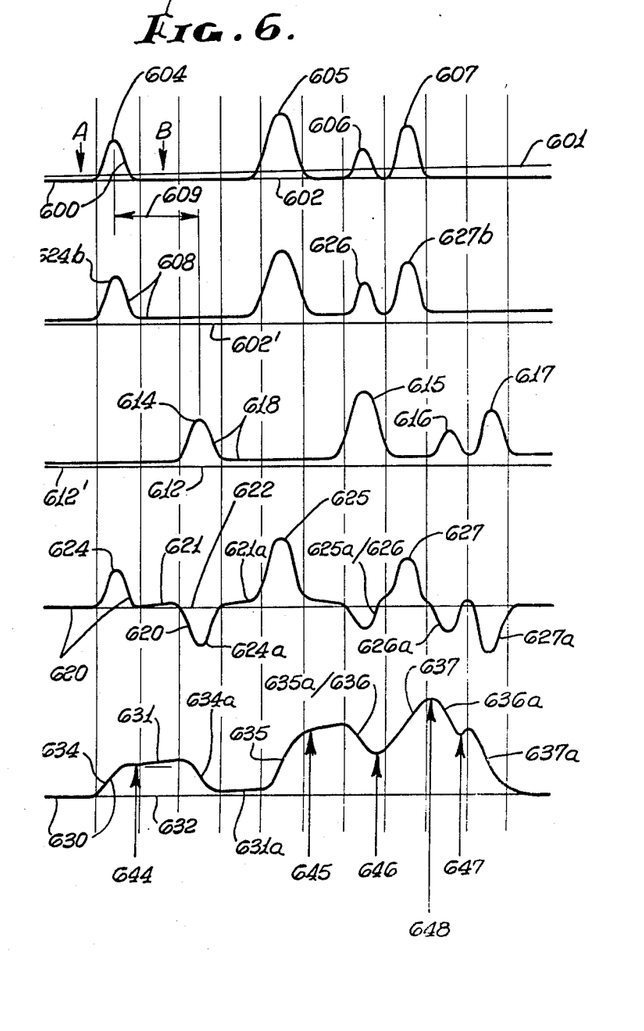
FIG. 6 is a signal diagram showing some time and signal-amplitude relationships involved in the signal-delay form of my invention.
Figure 6A:
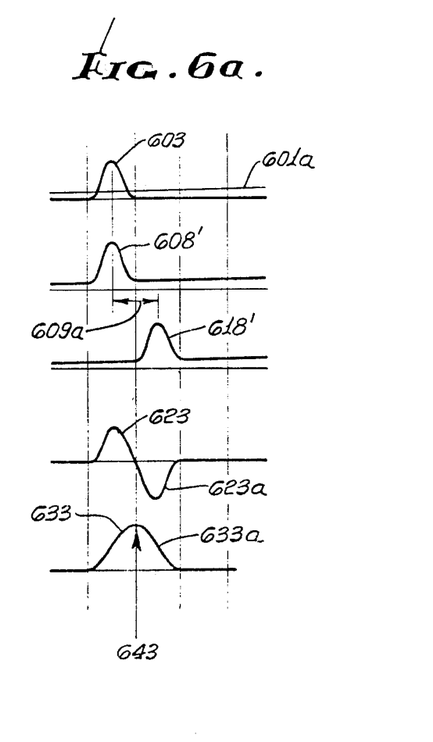
FIG. 6a is a special case of FIG. 6.

FIGS. 6 and 6a represent details of sample and contaminant concentrations in the measurement station 202 of FIG. 2, the resulting electrical signals at 206, 207 and 207a, and some possible versions of output signal 209 — all vs. time. In the top drawing of FIG. 6, the trace 600 represents actual concentrations of various sample constituents in measurement station 202, as such concentrations sequentially appear in the measurement station; the trace 601 represents concentration of contaminant material in the station during the sequential appearance of sample-constituent concentrations; and the line 602 represents the zero-concentration level. Thus peaks 604, 605, 606 and 607 represent respectively the successive appearances of various sample constituents in the station. The contaminant concentration level 601 is significant relative to the sample concentrations; and changes significantly in a way which is not obviously correlated with the sample concentrations; however, the contaminant concentration changes substantially less rapidly than the sample concentrations change. The significance of points A and B will be clarified below.

In the second drawing of FIG. 6, the trace 608 (relative to zero line 602') represents the "sum" signal 210 (of FIG. 2) which results from response of sensor 204 to concentrations 600 and 601 simultaneously. (For simplicity of discussion the signals are shown here and in FIGS. 6a, 6b, 7 and 7a as positive for higher concentrations, from a baseline level of zero; though in practice, depending on the type of detector used, the zero-concentration signal level may be nonzero and the presence of nonzero concentrations may reduce the signal level. The signal illustrated can be obtained from such actual detector-output signals by one inverting amplifier and dc offset.) It is this signal which is directly accessible to the analyst in prior-art systems; and the object of my invention is to eliminate the variable and unknown contaminant-generated component, giving access to information more directly related to unknown sample-constituent concentrations 600.

In the third drawing of FIG. 6, the trace 618 (relative to zero line 612') represents the delayed signal 207a which results from progress of signal 207 through delay device 205. This trace is of course substantially identical with trace 608 except for displacement to the right by the distance 609, whose significance has already been stated. The relationship between the waveshapes of 608 and 618 is very nearly the same as that between the shapes of signals 608 and 618 in FIG. 6 of my aforementioned copending application, except that in the present case the two waveshapes are substantially identical, whereas in my copending application, as mentioned above, the trace shapes are very slightly different, due to "mixing" in (referring now to FIG. 2 of that application) the measurement chambers 202 and 203 and flow path 210.

In the fourth drawing of FIG. 6, trace 620 shows the result of subtracting 618 from trace 608, within the signal processor 208 of FIG. 2. Positive peak 624 in effect results from peak 604 (see top drawing of FIG. 6), negative peak 624a from the later subtraction of the same peak 604. Nonzero intermediate segment 621 is a result of subtracting contaminant level 601 at time A, a time when the contaminant concentration is rising, from level 601 at later time B, when the concentration is higher (and still rising). Of course this slight residual error — much smaller than the overall contaminant concentration, and greatly exaggerated in the diagram — is also present at the peaks 624 and 624a. Clearly in this resultant signal the effects of contaminant concentrations are nearly absent — the only imperfections arising where significant changes in contaminant concentration occur during time intervals shorter than the interval corresponding to the distance 609. This illustrates the desirability of using the shortest signal delay which can effectively provide "time separation" of each sample constituent's respective appearances in the two measurement-signal versions 206 and 207a (which is to say traces 608 and 618).

The bidirectional signal pattern 620, as previously mentioned, may be bewildering to an observer who is not acquainted with the foregoing explanation. Moreover, if a signal peak such as 626 in trace 608 should happen to occur at about the same time as a concentration peak such as 615 in trace 618 — that is to say, if two constituents of the sample happen to be separated in the fluid stream by a time interval roughly equal to the signal delay 609 established at 205 — than the resultant trace 620 may not be easy to interpret in the overlap area, as at the peak marked 625a/626.

For these reasons I prefer to include in signal processor 208 an integrator, to derive from difference signals such as 620 an integrated signal such as 630, in the bottom drawing of FIG. 6. Rising segments such as 634 of trace 630 result from positive peaks 624 of trace 620, while falling segments such as 634a result from negative peaks 624a. Very slowly rising segments 631 and 631a result from very small residual offsets 621 and 621a, again pointing to the desirability of minimizing delay interval 609 to the extent practical. However, it must again be emphasized that these residuals are typically very small; in the drawings they have been exaggerated to permit clear illustration.

The heights of the nearly horizontal elevated portions of trace 630 are related to the sample constituent concentrations sought. Although some additional signal processing of these signals may be required to derive signals which are proportional to sample concentration, depending upon the type of sensor used, in this discussion for simplicity it will be said that these signals "represent" the sample constituent concentrations sought. For example the nearly flat peak 631 — or particularly its height at 644 — represents the sample concentration corresponding to peak 604; the flat-topped peak 645 represents the sample concentration corresponding to peak 605. It is of interest to note the integrating system behavior in instances where overlap occurs, as at 625a/626 mentioned earlier: here there are a distinct (elevated) trough 646, representing the sample concentration corresponding to peak 606, and a distinct, nearly flat inflection point 647, representing the sample concentration corresponding to peak 607. Intermediate flat-topped peak 648 represents the sum of the two concentrations represented respectively by 646 and 647.

If preferred, the integrator within processor 208 of FIG. 2 may precede rather than follow the differencing device within processor 208; or an integrator may be inserted between sensor 204 and the junction point of signals 206 and 207; or identical integrators may be inserted in both signal paths anywhere between that junction point and processor 208, all with the same resulting waveform 630 (or 633 to be discussed shortly) — since as is well-known the mathematical processes of integration and subtraction are commutative — and all within the scope of the appended claims.

The traces in FIG. 6a are a special case of traces such as those in FIG. 6. In FIG. 6a it is assumed that delay interval 609a is chosen to be roughly equal to, or slightly greater than, the half-height width of a typical sample peak, such as 603 — shown added to background 601a as 608'. Upon subtraction of similar but delayed peak 618' in signal 207a from peak 608' in signal 206, the resultant is bidirectional curve 623/623a, which has the general shape of the derivative of a Gaussian peak. Integration therefore produces curve 643 of very generally Gaussian shape, whose peak occurs halfway between the original peaks 603 and 613. The contaminant level is effectively suppressed as before (curve 630), but the flat-topped peak shape previously discussed is here replaced by a waveformm which is more traditional in general appearance.

If the delay is shortened appreciably relative to that of FIG. 6a, the heights of peaks 623, 623a, and 643 are reduced, producing a spuriously low measurement. Shortening the delay can also degrade accuracy because some constituents may exhibit more "tailing" than others; if the apparent concentration or amount as indicated by the integrated peak height is very sensitive to the exact shape of a peak, then the proper compensation for tailing may be difficult to determine for samples having variegated constituents. However, the short delay time has the advantage of more-accurate autocancellation of relatively rapidly changing contaminant levels. If the delay is lengthened appreciably, the shapes of FIG. 6 result. I personally prefer to arrange the system flow rate and the delay interval introduced at delay device 205 to obtain curve shapes such as those in FIG. 6a, though some adjustments are required to maintain this condition for various kinds of sample constituents — whose peak widths are correspondingly various.

Figure 6B:
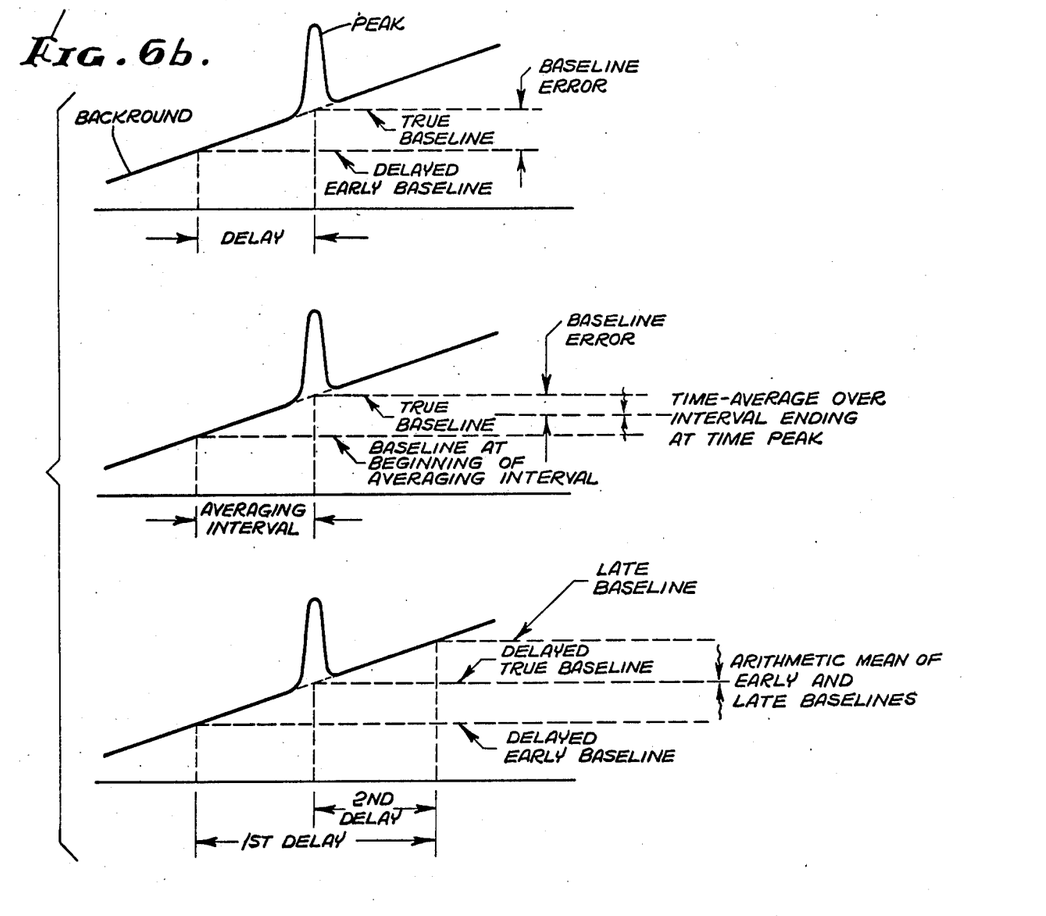
FIG. 6b is a signal-detail diagram, exaggerated for clarity, illustrating an advantage of combining three rather than only two signals in the signal-delay form of my invention.

Although the foregoing disclosure regarding the signal-delay form of my invention represents advances over prior art, and in some circumstances over the disclosure of my aforementioned patent, there are limitations on performance of systems constructed in accordance with the foregoing disclosure. FIG. 6b illustrates some of these limitations, and additional aspects of my invention which may be employed to overcome the limitations; in all of the diagrams in this figure the slope of the background is extremely exaggerated relative to the peak height and width, to simplify illustration; thus the effects illustrated are actually much weaker than indicated in the drawings, but are nevertheless significant when high analytical accuracy or sensitivity is desired.

The top view of FIG. 6b shows how a small "baseline error" (that is, an error in background-signal autocancellation) can occur in the signal-delay form of the invention when the background signal changes appreciably during the delay interval (that is, when the background signal has a large slope). The delay interval along the abscissa corresponds to a signal increment downward (for rising background, as illustrated) to the "delayed early baseline" from the "true baseline". The true baseline may be defined as the signal level, just below the center of the peak, which the background signal would exhibit if the peak were absent.

The second view of FIG. 6b shows how a baseline error can arise in the signal-averaging form of my invention when the background signal changes appreciably during the averaging time. This diagram is included here for completeness though it may not be clear to the reader until after the later portions of this disclosure which deal with the signal-averaging form of my invention have been read. The average background-signal value, for unchanging slope, is generally half as far from the true baseline as the signal increment corresponding to the full averaging interval. In this diagram the time scale (abscissa) is greatly compressed relative to that in the top and bottom diagrams of FIG. 6b; the ideal averaging interval here is much longer than the ideal delay interval. Consequently the baseline error here can be quite large.

The bottom drawing of FIG. 6b shows how the arithmetic mean of two symmetrically-placed measures of the background signal yields an exact measure of the true baseline, for autocancellation as previously and hereinafter described — provided that the background signal is changing at a constant rate.

To implement this concept it is necessary to apply a first delay to the early baseline measure, and a second delay — about half as long — to the peak signal, before finding the mean of the "early" and "late" baselines and subtracting the mean from the delayed peak signal. (The terms "mean" and "arithmetic mean" are used in this connection rather than the term "average", to maintain the distinction between this special case of the signal-delay form of my invention and the signal-averaging form of my invention discussed elsewhere in this disclosure.)

The resulting waveform is advantageous in offering more-exact background autocancellation, and in simplifying the interpretation of the record in the absence of integration, provided the overlapping peaks are avoided. It may be somewhat disadvantageous in that the number of negative-going peaks resulting from subtraction of the mean of the complete early and late signals is twice the number in the basic signal-delay system previously described and each negative-going peak in the system now under discussion is just half the height of the corresponding positive-going peak, complicating the interpretation of signals by integration. Nevertheless, where best precision and accuracy are required this may be the best method.

Figure 2A:
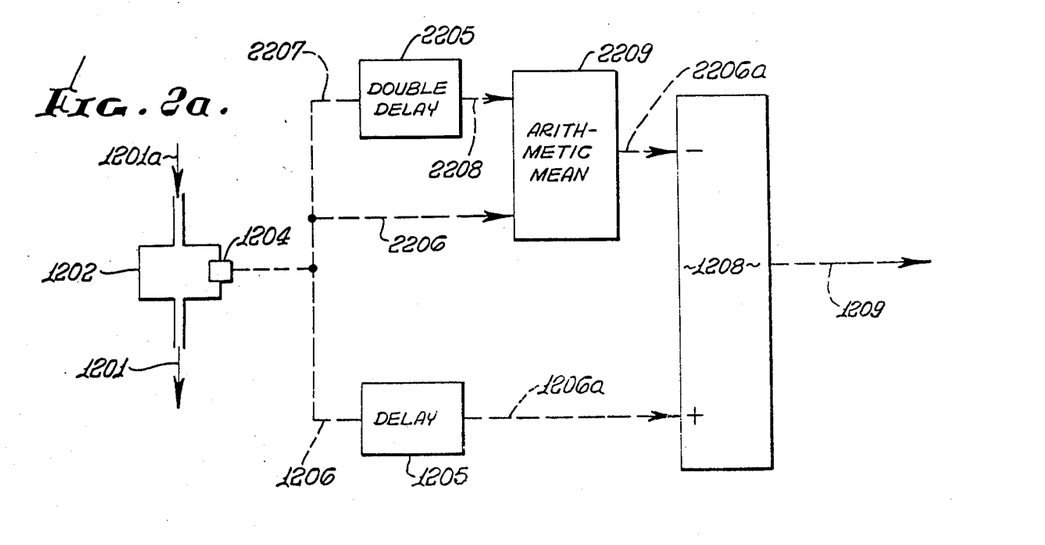
FIG. 2a is a special case of FIG. 2, illustrating the combining of three rather than only two signals in the signal-delay form of my invention.
Figure 3:
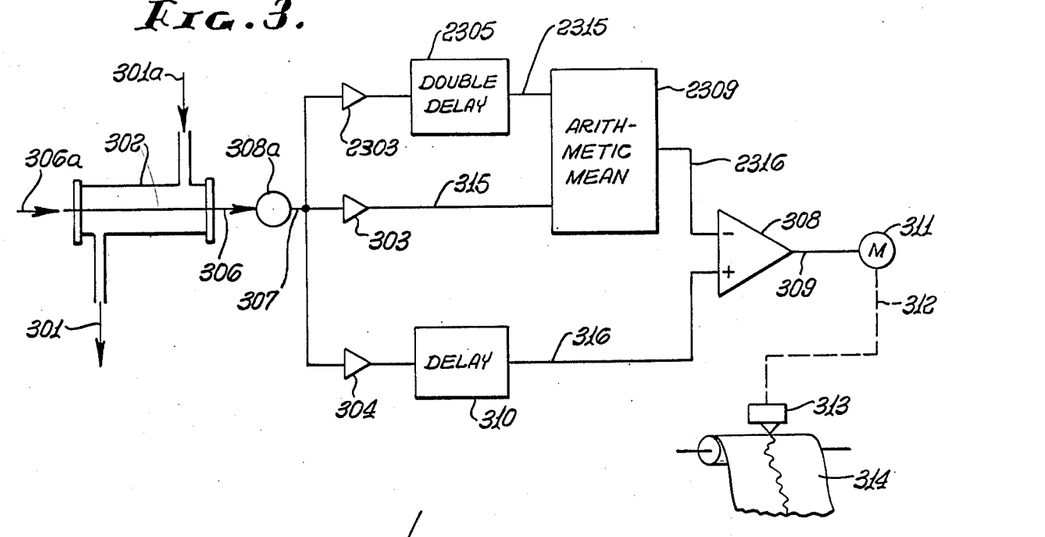
FIG. 3 is an example of the principle of FIG. 2a using absorption spectrometry as detection medium.

The concept illustrated in the bottom view of FIG. 6b corresponds to the apparatus shown in FIGS. 2a and 3.

FIG. 2a represents a variant of FIG. 2 wherein three versions of the signal are combined, rather than only two. In this drawing, elements 1201a, 1201, 1202, 1204, 1206, 1208 and 1209 are the same in form and general function as the correspondingly numbered elements of FIG. 2 — but here even the main signal path, that which passes directly to 208 in FIG. 2, is provided with a delay device 1205, supplying a delayed version at 1206a to the processor 1208; while the signal applied at 2206a to the processor 1208 for subtraction from the main signal at 1206a is obtained by finding the arithmetic mean at 2209 of an undelayed signal at 2206 and a signal at 2208 which has been subjected at 2205 to a delay which is twice as long as that introduced in the main signal at 1205. The two signals 2207 and 2206 used in devices 2205 and 2209 to generate the arithmetic mean signal at 2206a, and the signal at 1206 used to generate the delayed main signal at 1206a, are all three the same output signal from sensing device 1204.

This apparatus provides that the main signal at 1206a (delayed) is compared with a mean signal 2206a taken symmetrically forward and backward in time from the instant of the main signal at 1206a — the condition shown in the bottom drawing of FIG. 6b. In effect the mean signal is a delayed signal whose mean delay is zero.

FIG. 3 represents in more specific terms the signal-delay form of my invention. Here the measurement station is a flow-through optical cell 302, provided with optical-quality end windows for entrance of infrared (or other radiation) measurement beam 306a, and exit of such beam (after attenuation by any sample or contaminant present) at 306. The fluid stream for analysis enters cell 302 at 301a and leaves cell 302 at 301.

In FIG. 3 it is tacitly assumed that 306a is a beam of restricted or frequency-correlated wavelength, coming from a monochromator, interferometer, filter, or line-radiation source, and that 308a is a detector (producing an electrical signal 307 in response to radiation signal 306); however, with appropriate optical-path modifications the wavelength identification may be accomplished after the beam passed through the cell, in conjunction with detection or electronic processing as at 308a or 308. Beam 306a (and consequently 306) may be periodically interrupted or modulated, by means well-known in the art, so as to permit ac amplification and synchronous rectification of the signal 307. In any event the sensor 204 of FIG. 2 is here represented by measurement optical beams 306a and 306, and optical detector 308a, as well as the radiation-passing end windows of cell 302.

It should also be noted that the radiation beam of FIG. 3 may be repetitively scanned through a range of wavelengths, if it is rendered monochromatic by a monochromator, or its various wavelength components may be repetitively modulated at various frequencies by an interferometer, so as to generate a signal 307 which contains spectral absorption information to allow characterization of the absorbing substances passing through cell 302. Such information may allow or facilitate identification of the molecular species that produce a given peak in absorption. Also the signals may in these cases be combined without further processing, or they may each be converted into percent transmission versus wavelength by taking their ratio with respect to a signal derived from an unabsorbed reference beam, as is ordinarily practiced in spectrophotometry, or they may be converted into the negative logarithm of the transmission fraction by well-known means, to obtain signals proportional to concentration of the optical absorber, also as is conventional in spectrophotometry. Furthermore, if the signals arise from a beam modulated by an interferometer, they may be delayed and combined as interferograms and the resulting combination signal subsequently converted into a spectrum, or they may be preprocessed by inverse Fourier transformation prior to delay and combination, all following well-known practices in this art.

In the embodiment shown, electrical signal 307 proceeds to substantially identical preamplifiers 303, 2303 and 304, whence the output of preamp 2303 after extended delay at 2305 proceeds at 2315 to one input of an arithmetic-mean device 2309, and the output of preamp 303 proceeds at 315 directly without delay to the other input of the arithmetic-mean device 2309. At 2316 the arithmetic mean of the two input signals 2315 and 315 is applied to one input of the amplifier 308, and the output of preamp 304 after delay at 310 is applied to the other input 316 of amplifier 308. The amplifier 308 subtracts the input at second terminal 316 from the input at first terminal 315, and/or otherwise processes these two electrical signals to create output signal 309, the embodiment of signals 9 in FIG. 1 and 209 in FIG. 2, which may have a waveform such as 620 or 630 in FIG. 6, or the corresponding waveforms of FIG. 6a; or which may be relatively unprocessed if preferred. This output signal is directed to appropriate utilization means, such as a motor 311 which by a mechanical linkage 312 controls the transverse position of a recording pen 313 on continuously advanced chart paper 314.

While a long delay introduced in the delay means 310 and 2305 produces waveforms analogous to those illustrated in FIG. 6, my personal preference is for delay devices which introduce a relatively brief delay — to obtain waveforms analogous to those of FIG. 6a. It is within the compass of my invention to provide delay devices 310 and 2305 in the form of purely electronic delay lines, or relative-physical-motion storage-and-retrieval systems such as tape or disc recording and playback, or a digital-logic storage-and-retrieval system, or combinations of these three kinds of devices, or indeed any delay-effecting means which have input-output "tracking" fidelity adequate to the precision and accuracy requirements of the particular application at hand. In any case it is to be understood that the "double delay" introduced at 2305 is to be twice the "delay" interval introduced at 310, inasmuch as the two signals are combined in arithmetic mean proportions at 2309 to obtain a reference signal whose effective mean delay is zero with respect to the main signal 316; it is of course possible and within the scope of my invention to use delay times in other proportions than 2:1, provided that a suitably weighted mean is then taken at 2309, so that the effective mean delay is zero, but this added complexity would not appear to earn any functional advantage.

Figure 4:
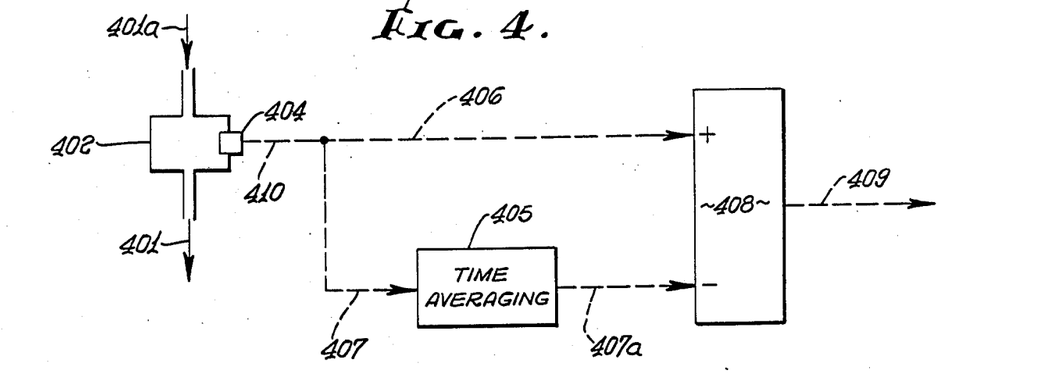
FIG. 4 is a schematic representation showing the signal path of the signal-averaging form of my invention.

In FIG. 4, representing the signal-averaging form of my invention, fluid enters and leaves the measurement system at 401a and 401, respectively, traversing as before measurement station 402 with its sensing means 404, which produce signal 410 for application at 406 directly to the processor 408, and for application at 407 to an input of averaging device 405, whence a time-averaged signal appears at processor input 407a. The two inputs 406 and 407a, with subtractive or other appropriate processing at 408, produce an output signal directed at 409 to utilization means (not shown) such as previously described.

This schematic appears similar to that of FIG. 2; here however the time-distortion device 405 between signal lines 407 and 407a is an averaging device rather than a delay device such as 205 in FIG. 2. The averaging device performs a function analogous to the dilution chamber disclosed in my aforementioned patent (element 410 in FIG. 4 of that patent), namely to generate a measurement-signal version which is some kind of time average of the measurement signal 410, taken over a time interval which is longer than the duration of the presence of any sample constituent (i.e., the constituent's "residence time") in the measurement station 402.

As the averaging interval is thus long compared with the duration of any sample-constituent peak in the measurement signal 410, the peak component of measurement-signal version 407a which is attributable to each sample constituent at measurement station 402 is a small fraction of the component of the signal peak at 410 and 406 attributable to that same constituent.

In fact the contribution of a given constituent to the signal version 407a — and the resulting peak-height residual relative error in the difference signal 409 after subtraction of 407a from 406 — is substantially equal to the ratio of (1) that constituent's residence time to (2) the averaging time in the device 405.

This leads to a variety of ways of using the signal-averaging form of my invention — all having different advantages suited to different measurement requirements.

For example, by averaging over intervals which are hundreds or even thousands of times as long as the longest residence time of sample constituents involved, the fractional error in peak height in signal 409 may be made negligible — a few thousandths or ten-thousandths. Of course this accurately quantitative utilization of my invention requires very slowly changing contaminant concentrations.

On the other hand, by averaging over intervals just two or three times as long as the longest residence time, the spectral interference of strongly absorbing contaminants with complex spectra can be suppressed sufficiently, relative to the spectral structure of sample constituents, to permit identification of the constituents; it should be borne in mind that, while the contaminant concentrations indicated in the accompanying figures are smaller than the sample constituent peaks indicated, the opposite may be true in a particular case. Such purely qualitative analysis can be supplemented with a rough quantitative value too, because a first-order correction of the observed peak heights is readily applied, on the basis of the observable residence time and the known averaging time: if the ratio of these two times is called $f$, then the relative error in peak height is $f$ and the correct peak height is approximately the observed peak height divided by $1-f$.

In any case this method has the advantage of avoiding the negative-going peak(s) associated with the signal-delay method.

Figure 7:
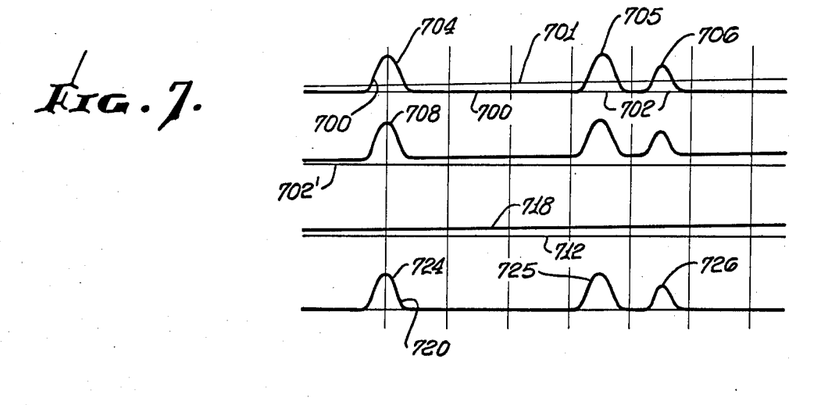
FIG. 7 is a signal diagram showing some time and signal-amplitude relationships involved in the signal-averaging form of my invention.

FIG. 7 represents details of sample and contaminant concentrations in the measurement station 402 of FIG. 4, the resulting electrical signal at 406 and 407, and a corresponding possible version of output signal 409 — all vs. time. In the top drawing of FIG. 7, the trace 700 represents actual concentrations of various sample constituents in measurement station 402, as such concentrations sequentially appear in that measurement station; trace 701 represents concentration of contaminant material during the sequential appearance of sample-constituent concentrations; and the line 702 represents the zero-concentration level. Thus peaks 704, 705 and 706 represent respectively the successive appearances of various sample constituents in the station. The contaminant concentration level 701 is significant relative to the sample concentrations; and changes significantly in a way which is not obviously correlated with the sample concentrations, but substantially less rapidly. The requirement for slowness in contaminant-concentration variations is more stringent for the signal-averaging form of my invention than for the signal-delay form — the exact degree of stringency depending upon the degree to which quantitative vs. qualitative results are sought, as explained in the foregoing paragraphs.

In the second drawing of FIG. 7, the trace 708 (relative to zero line 702') represents the "sum" signal 410 (of FIG. 4) which results from response of sensor 404 to concentrations 700 and 701 simultaneously. Again, it is only this signal which is accessible in prior-art systems; and the object of my invention is to eliminate the variable and unknown contamination-generated component.

In the third drawing of FIG. 7, the trace 718 represents the time-average signal at 407a in FIG. 4, obtained by passing the signal 708 (i.e., 410) through averaging device 405; the line 712 represents the zero signal level to which signal 708 is referred. Because the averaging period of device 405 is greater than the duration of any one sample constituent peak, the sample-constituent-generated amplitude of signal 718 at 407a (and proceeding into processor 408) is correspondingly lower than the sample-constituent-generated peak amplitudes in signal 708 at 406; and this is true at all times for all sample constituents other than contaminants.

The averaged trace 718 is merely the long-time average value of trace 708; hence it may be extremely close to the (unknown) level of contaminant trace 701, in cases wherein the sample peaks in trace 708 are relatively infrequent (or small). The average value represented by trace 718 is "smeared out" over a long averaging period and is also delayed, relative to trace 700, by a long interval related to the averaging period; however, to the extent that the sample-constituent component of signal 718 may be considered negligible, the delay applied to changes in these concentrations is of no consequence.

The contaminant-concentration component of signal 718 is similarly averaged and delayed to produce a component of signal 718 at 407a; however, since the contaminant component tends to be representable as generally a smooth, nearly-horizontal trace 701 the averaging process does not greatly affect the concentration accuracy. To the extent that the contaminant concentration can be considered to change only negligibly during the averaging time of device 405, the trace 701 and the contaminant-generated component of trace 718 are substantially identical — so that subtraction of sum waveform 718 from sum waveform 708 yields "difference" waveform 720 wherein contaminant concentrations are accurately cancelled. If, as previously indicated, the sample-constituent-generated component of trace 718 is negligible, then trace 720 represents purely the sample-constituent concentrations at station 402.

As previously noted, this representation is of excellent simplicity and straightforwardness — but fails in its accuracy if the contaminant concentrations change significantly within time intervals comparable to the averaging time of device 405. Particularly in the case of temperature-programmed gas-chromatograph columns this limitation is often significant, as coating bleed can change significantly in minutes; applicability of the dilution method to individual circumstances must therefore be determined with great care.

It should be understood that in FIG. 7 the slopes of traces 701 and 718 are exaggerated, relative to the amplitudes and the number of the peaks 704, 705 and 706, to permit clarity of illustration. Further, particularly with regard to quantitative applications of my invention, the frequency of peak occurrence is exaggerated, relative to the peak widths, also for purposes of illustration. As has already been stated the averaging time for highly accurate quantitative results must typically be at least several hundred times the effective width of any sample peak, and the peaks must be widely separated in time and/or very narrow and/or shallow, to render the sample-constituent component of trace 718 negligible.

Valuable qualitative results are obtainable under less-stringent conditions, as previously explained.

Figure 7A:
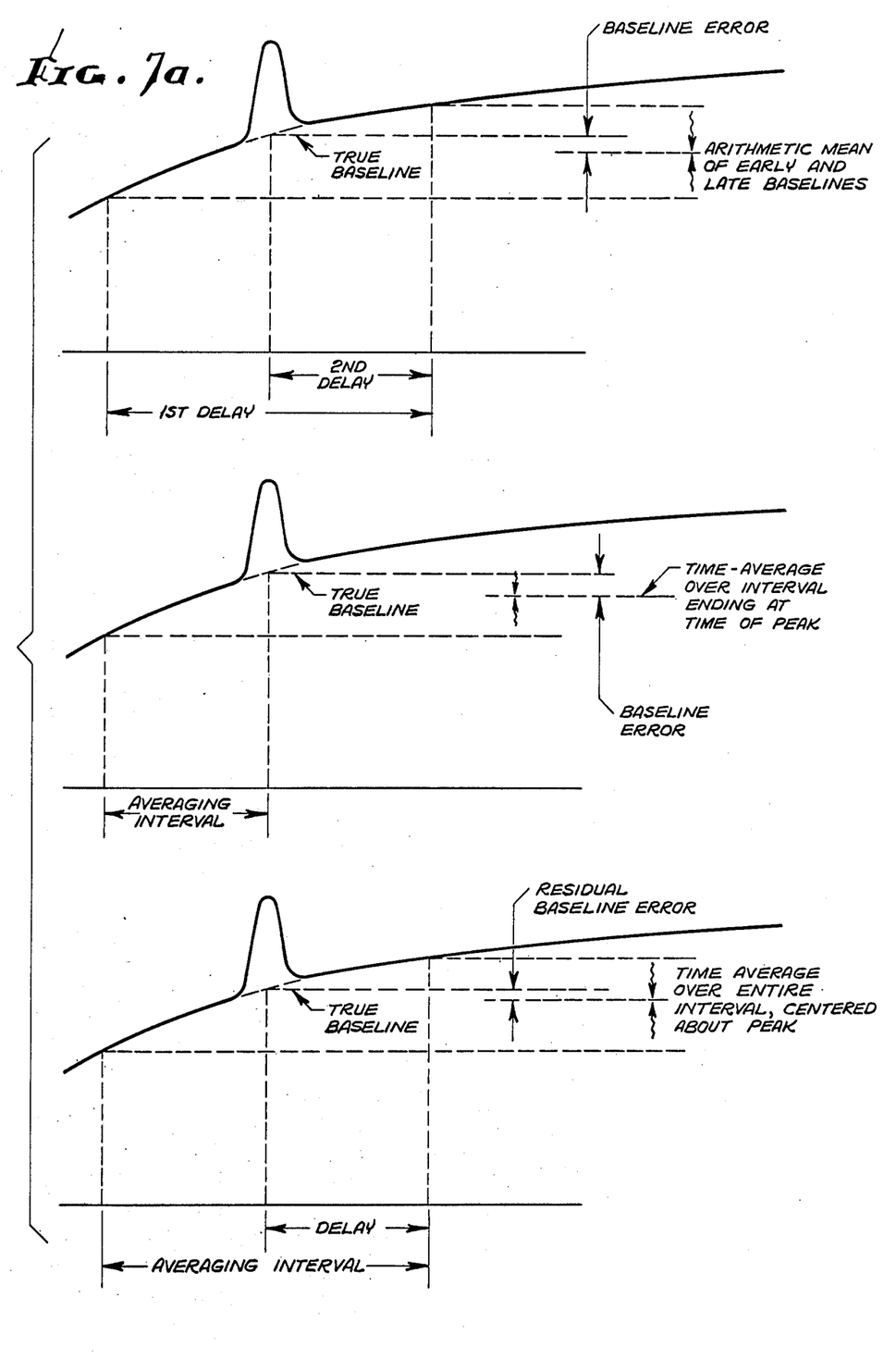
FIG. 7a is a signal-detail diagram, exaggerated for clarity, illustrating an advantage of delaying the main general version when using the signal-averaging form of my invention.

Although the foregoing disclosure regarding the signal-averaging form of my invention represents advances over prior art, and in some circumstances over the disclosure of my aforementioned patent, there are limitations on performance of systems constructed in accordance with the foregoing disclosure. FIG. 7a illustrates some of these limitations, and additional aspects of my invention which may be employed to overcome these limitations; in all of the diagrams of this figure, the slope of the background is extremely exaggerated relative to the peak height and width, to simplify illustration; thus the effects illustrated are actually much weaker than indicated in the drawings.

It has already been shown in FIG. 6b, and the disclosure accompanying it, how rapid change of background signal can introduce a small error, and how using the arithmetic mean of two background signals — one "early" and one "late" — can eliminate such error provided that the background signal is changing at a constant waveform slope).

FIG. 7a now illustrates for the case of a background signal which is not changing at a constant rate how even the baseline found by the arithmetic-mean-of-two-background-signals concept can fail to be exactly equal to the true baseline. (it must be emphasized that the mean-of-two-reference-signals method always produces a more accurate measurement than the signal-reference-signal method, and so the error in the mean-of-two-signals method is typically very small.) The simple signal-averaging approach may generate a larger error (though still very small), as shown by the second drawing in FIG. 7a, partly because of the longer time interval necessitated in this method and partly because the averaging time is entirely prior to the peak.

When the background-signal slope is changing, assuming that the overall or steepest slope is not too steep for the signal-averaging form of the invention, it may be desirable to use the signal-averaging form but to use an averaging interval which is symmetrically disposed about the peak. (This may produce the most accurate contaminant autocancellation, but will as previously explained be subject to a relative error in sample-constituent peak heights. Thus this method may be best suited to small and/or infrequent sample-constituent peaks, superimposed on a very large contaminant level which is changing rapidly and nonlinearly with time, and in situations wherein qualitative results are sought.)

This is similar to the mean-of-two-background-signals concept but here the entire interval, not just the end-points, is used for a continuous time-averaging. In practice this requires delaying the peak by a time interval equal to half the averaging interval, as shown in the bottom drawing of FIG. 7a. This corresponds to the equipment illustrated in FIGS. 4a and 5.

Figure 4A:
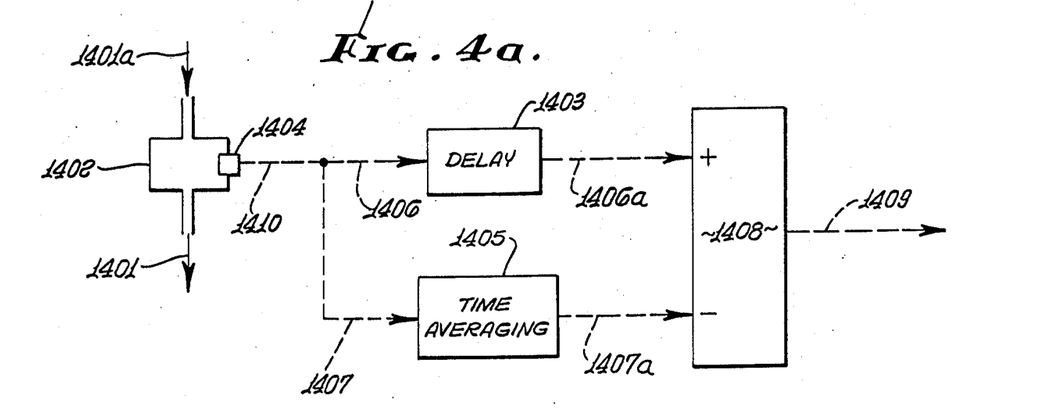
FIG. 4a is a special case of FIG. 4, illustrating delay of the main signal version when using the signal-averaging form of my invention.

FIG. 4a represents a variant of FIG. 4 wherein signal averaging is introduced into one signal path — just as in FIG. 4 — and signal delay is introduced into the other signal path.

In FIG. 4a, elements 1401a, 1402, 1401, 1404, 1410, 1406, 1407, 1405, 1408 and 1409 are the same in form and general function as the correspondingly numbered elements of FIG. 4; but delay device 1403 delays signal passage from its input 1406 to the input 1406a of processor 1408, by a delay interval substantially half the averaging period, so that in effect the unaveraged signal (delayed) at 1406a is compared with a time average signal 1407 a taken symmetrically forward and backward in time from the instant of the unaveraged signal at 1406a. This minimizes the constraint (mentioned earlier in connection with FIG. 4) this the contaminant concentration change only negligibly during the averaging time of device 405 in FIG. 4. In fact the contaminant concentration may change substantially during the averaging period provided that the rate of change of the contaminant concentration changes fairly slowly relative to the averaging period; straight-line changes (i.e., constant rate) of contaminant concentration produce no error at all — except, of course, for the peak-height errors resulting from overly large ratios of residence time to averaging time, as previously explained.

Figure 5:
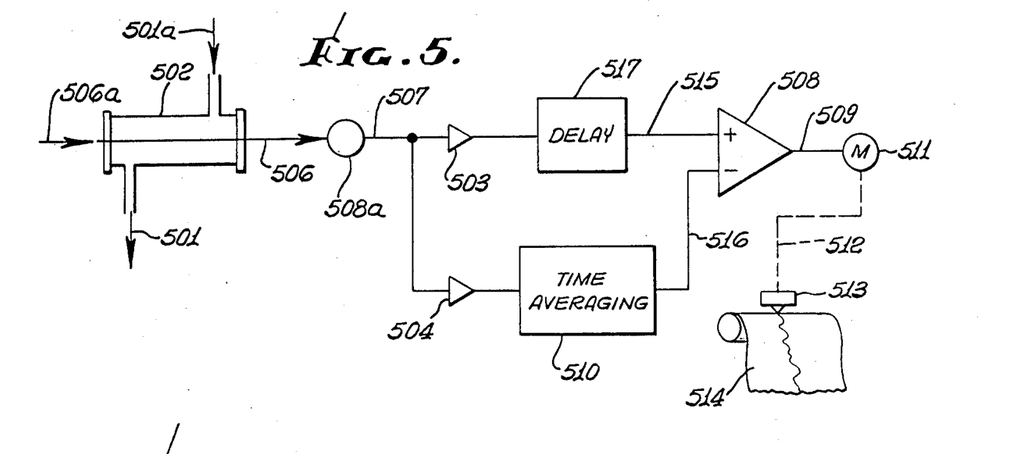
FIG. 5 is a more-detailed illustration exemplifying the general system of FIG. 4a, using absorption spectrometry as a detection medium.

FIG. 5 represents in more specific terms the signal-averaging form of my invention, with signal delay to minimize constraints on rate of contaminant-concentration change as in FIG. 4a. Here the measurement station is a flow-through optical cell 502, provided with optical-quality end windows for entrance of infrared (or other light) measurement beam 506a, and exit of such beam (after attenuation by any sample or contaminant present) at 506. The fluid stream for analysis enters cell 502 at 501a and leaves cell 502 at 501.

In FIG. 5 it is assumed that 506a is a beam of restricted wavelength and 508a is a detector producing an electrical signal in response to possibly attenuated beam 506 — also of restricted wavelength; however, wavelength identification may be instead accomplished after the beam passes through the cell. The beam is suitably interrupted periodically, to permit frequency- or even phase-sensitive detection.

In any event the sensor 404 of FIG. 4 is here represented by the optical beam at 506a and 506, the detector 508a, and the radiation-passing end windows of the cell 502.

In the embodiment shown in FIG. 5, electrical signal 507 proceeds to identical preamplifiers 503 and 504, and from preamp 503 to delay device 517 —which performs the function of device 403 in FIG. 4a — and from preamp 504 to averaging device 510 —which performs the function of device 1405 in FIG. 4a. The delayed output at 515 and the averaged output at 516 are applied to amplifier 508, which subtracts the averaged signal from the delayed signal and/or otherwise combines the two input signals to create output signal 509, the embodiment of signals 9 in FIG. 1 and 409 in FIG. 4, which may have a waveform such as 720 in FIG. 7; or which may be relatively unprocessed if preferred. This output signal is directed to appropriate utilization means, such as a motor 511 which by a mechanical linkage 512 controls the transverse position of a recording pen 513 on continuously advanced chart paper 514.

Suitable time-averaging devices 510 may be R-C filters, in which case the desired delay interval at 517 is related in a conventional fashion to the time constant of the filter; or digital-logic averaging may be employed, or other types of apparatus or combinations of any of the above will serve as dictated by requirements of the application at hand.

It is to be understood that all of the foregoing disclosure applies equally well to liquid and gaseous fluid streams. Where fluid chromatographic columns are used preliminarily to disperse sample constituents in time for analysis, my invention is useful to equivalent advantage in both gas and liquid chromatographs.

Figure 8:
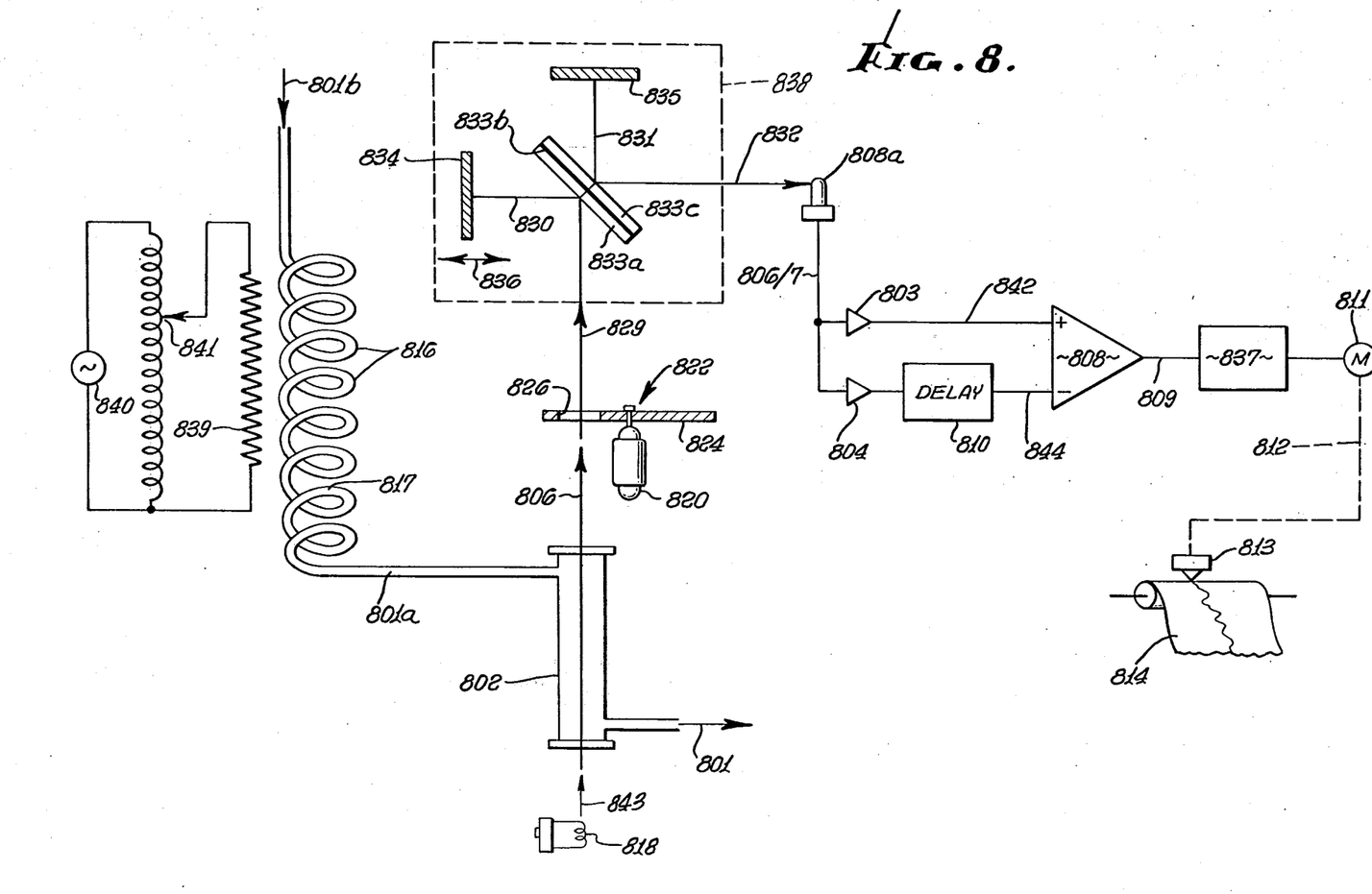
FIG. 8 is a schematic representation of a specialized embodiment of my invention in gas chromatographic analysis, with detection by interferometric infrared spectrometer. The series signal-delay form is involved.

FIG. 8 shows an application of the signal-delay form of my invention to the optical monitoring of gas-chromatograph effluent. This signal-delay system is related to that of FIG. 3, but here spectral information is isolated following the sample cell, along the optical path, rather than prior to point 306a along the path as in FIG. 3.

In FIG. 8 a gas sample to be analyzed is typically injected as a narrow slug into a carrier gas stream which flows continuously into the system at 801b. The gas first enters chromatographic column 816, in which there is an elongated chamber which may have coated upon its inner surface 817 an extended film of "stationary phase" material — in which the sample constituents are differentially soluble. Alternatively, the elongated chamber 816 may contain appropriate "packing" material to provide an extended surface for adsorption, or for retaining an extended film of stationary phase material as a coating in which the sample constituents are differentially soluble, all as is well-known in the art. (For simplicity hereinafter and in the appended claims the term "coating" is used to refer to the coating upon the internal wall of the column, or upon the packing if such be in use; or the packing itself.)

As a result, in either case (direct coating or packing), various sample-gas constituents pass at various rates through the column, therefore entering tube section 801a separately at various times after injection of the sample at 810b, so that they are separated in time for individual analysis.

Due to gas mixing (diffusion of each sample-constituent slug in both directions in the carrier-gas stream), the individual constituents do not enter tube 801a as perfect slugs, their concentrations instead varying with a very-generally Gaussian-curve dependence on time — as previously illustrated (FIGS. 6, 6a and 7).

As a commonly practiced, the column is equipped with an oven or heater as symbolized at 839 — with electrical power application at 840 — programmed for gradual increase, to facilitate the passage of more-strongly adsorbed components is convenient time interval, by adjustment of oven or heater power as at the autotransformer 841.

The gas entering tube 801a comprises, in addition to the gas entering the chromatograph chamber or "column" at 801b, some gaseous material which is evolved from the coating. Such so-called bleed material is evolved more copiously at elevated temperatures; thus as the autotransformer 841 is manipulated to expedite passage of slower gases the bleed contamination concentration increases. It is a changing contaminant concentration such as this which gives rise to the principal need for my invention, and particularly the signal-delay form thereof.

In the preferred embodiment of my invention illustrated in FIG. 8, gas from the chromatographic column proceeds to a photometric-cell analysis system, comprising optical cell 802. From this cell the gas is exhausted at 801.

To effect measurement, the system causes infrared radiation from source 818 to traverse cell 802 to conventional Michelson-type analyzing interferometer 838, the resultant radiation then proceeding to detector 808a.

Many specific sample-optical-path arrangements may be used to essentially equal advantage, but the system illustrated is usable. In this system synchronous motor 820 rotates disc 822, which has an opaque half-circle section 824 and a transmissive half-circle sector (e.g., aperture) 826. This disc is so oriented and rotated as to periodically interrupt the beam 843 from the glower or other source 818 (after passage through the cell 802) at the surface 824 of the disc 822; and alternately to pass the beam 843 from the glower or other source 818 (after passage through the cell 802) through the transmissive sector 826 of the disc 822 for projection into the interferometer 838.

The periodic interruption or "chopping" of the beam provides a cyclically recurring zero-transmission reference level. The frequency and phase of the rotation of disc 822 are advantageously synchronized with detecting electronics 803, 804 and 808 to be discussed hereunder.

As described in my aforementioned patent, incorporated herein by reference, the interferometer and detector generate an interferogram signal 806/7.

The electrical signal 806/7 from the detector is directed, after suitable amplification and preliminary processing in matched preamplifiers 803 and 804, into the opposite-sign-input terminals of differential amplifier 808, with the signal from one preamplifier 804 also passing through a delay device 810 enroute to the input of amplifer 808.

The differential amplifier 808, operating in conjunction with delay device 810, provides autocancellation of signal components due to contaminants in the sample gas stream, as do amplifier 308 and delay device 310 of FIG. 3. The output signal from amplifier 808 proceeds along a signal path 809 to a computer 837 — which is not illustrated) from mechanisms (not illustrated) which monitor the motion of the movable mirror 834 and/or the chopping disc 822.

Coordination mechanisms and utilization means such as those at 811, 812, 813, and 814 are described in my aforementioned patent.

It is generally preferable that the rotating disc 822 be made to complete a large multiplicity of rotations during each full excursion of the movable mirror 834, so that it produces a frequency outside the band of modulation frequencies generated optically by the moving mirror — so that rather than sacrificing continuity of the absorption information vs. time, there is a small loss of available signal due to the fact that the average radiation intensity is halved by the chopper.

A discussion of the opposite relationship of mirror-modulation and chopper-modulation frequencies appears in my aforementioned patent.

If preferred, the FIG. 8 system may be operated just as well with the interferometer preceding the sample cell, in the arrangement of FIG. 3.

If integration of the amplifier output signal 809 is to be employed, as previously discussed, such integration is best performed numerically by computer 837, which also must perform the absorption-wavelength correlations required to produce a spectrum; apply corrections for wavelength dependence of source intensity, detector sensitivity, system-optics transmission, and interferometer efficiency; and perform in some instances many other computations such as those required to identify a constituent and to derive concentration data from the difference data received.

For adjustment of critical-delay timing to obtain waveforms such as 623/623a of FIG. 6a, the signal-delay device 810 may be made adjustable as to duration of the delay which it introduces.

It will be understood that spectrometric devices (such as the combination of glower 818, cell 802, chopper 822, interferometer 838, detector 808a and the associated apparatus; or other types of spectrometer) may be of the balanced-beam type, provided with an additional optical cell filled with, for example, pure carrier gas, to provide a 100%-transmission or zero-absorbance reference signal. If desired, the beam may be switched in alternation between a path which passes through the 100%-transmission reference optical cell and the sample cell, so that the interferometer or other detection stage receives reference and sample optical signals in alternation, and thus can generate output signals which are normalized for source intensity, detector sensitivity, and condition of most of the optical system.

The data-interpretation discussions previously presented with regard to FIGS. 1 through 7 do not fully cover all the potential benefits of my background-signal-autocancellation invention, because the signals discussed are presented, for simplicity of discussion, as two-dimensional signals: signal amplitude vs. time. Many devices which may be used as sensing means, including spectrometric devices such as those of FIGS. 3, 5, 8 and 9, are in general capable of deriving what may be regarded as three-dimensional output information — i.e., signal amplitude vs. time and a second independent spectroscopy parameter, such as wavelength, molecular mass, electron-spin frequency, or nuclear magnetic resonance frequency, all of which are of course well-known in the spectroscopic arts. In the case of optical spectroscopy the "sensing means" may of course measure emissin, absorption, fluorescence or scattering; and various devices may be used to isolate various wavelengths, either at fixed positions singly or multiply, or scanning.

When such three-dimensional information-deriving capabilities are put to use in fluid-stream analysis — aided, for example, by liquid- or gas-chromatograhic sample-constituent separation — then such instruments become much more useful for qualitative as well as quantitative analysis. That is to say, such instrumentation can be used much more readily to determine what constituents are in a given sample of initially unknown makeup, as well as to determine the quantities of such constituents.

However, when instrumentation is used in such ways then the adverse effects of slowly changing contaminant concentrations can become much more significant than merely the degradation of measurement precision in correspondence with relative concentration. This is because contaminants can (and in practical cases often do) have complex spectral structure, and may have some spectral features which are "strong", relative to sample-constituent spectral features, to an extent which is out of proportion to their relative concentrations.

Such contaminant spectral structure is easily confused with, and masks or conceals, the spectral features of many possible sample constituents of interest — particularly, but not necessarily, if such possible constituents are present in relatively low concentrations.

My invention permits effective autocancellation of such complex and/or strong contaminant spectral structure, in just the same way, spectral point by spectral point, as described hereinabove with respect to "two-dimensional" contaminant-signal autocancellation, thereby rendering qualitative analysis of fluid samples by analytical means such as gas chromatography and infrared interferometric spectrometry much more effective.

Although considerable discussion of interferometric analysis appears herein, my invention is not limited to such techniques and is also useful in improving the performance of more-conventional spectrometric devices including mass spectrometers and ordinary absorption spectrometers. In the latter case, output signals produced by the instruments' standard circuits may be subjected to additional data processing as in an attached computer to introduce appropriate delays and compute difference data for integration (if desired) and finally reconversion to absorption or concentration information.

Moreovr, as noted earlier, my invention has broad applicability to analysis of many kinds of fluids including liquids, and by many kinds of concentration-monitoring devices other than optical-attenuation detection systems.

In interpretation of the appended claims in view of the foregoing disclosure it should be borne in mind that terms such as "signals" may under some circumstances include optical signals as well as electrical and other types of signals; and that "signal-processing means" may under some circumstances include all or part of optical systems which effect subtraction or other comparison or processing of such optical signals.

I claim:

1. A system for monitoring a first constituent in a fluid stream, which stream may also inclue a second constituent whose concentration in the stream changes slowly relative to the changes in concentration of the first constituent, comprising:
   a monitoring station, having sensing means for deriving a first component of a first measurement signal in quantitative response to presence of such first constituent in the station;
   said sensing means also deriving an additional component of such first measurement signal in quantitative response to presence of such second constituent in the station, such additional signal component constituting a spurious signal component;
   flow means, connected to the fluid stream and the monitoring station, for directing fluid from the fluid stream through the station;
   primary signal-processing means, connected to receive the first measurement signal from the sensing means, for deriving in response to the first measurement signal a second measurement signal which has a first component and an additional component corresponding respectively to the first and additional components of the first measurement signal, said primary signal-processing means comprising:
   signal-splitting means, connected to receive the first measurement signal from the sensing means, for generating a pair of intermediate signal versions in response to the first measurement signal, each having substantially the same sequence of amplitudes and frequencies as the first measurement signal, but each independently being subject to displacement in time relative to the first measurement signal;
   first delay means, connected to receive the two intermediate signal versions from the signal-splitting means, for establishing a relative time delay between the two intermediate signal versions; said relative time delay being substantially consistent and not directly controlled by any of the signals; and
   combining means, connected to receive the two intermediate signal versions with the said relative time delay, for generating the said second measurement signal by additive combination of the two intermediate signal versions in specified proportions;
   secondary signal-processing means, connected to receive the first measurement signal along a signal path from the sensing means and the second measurement signal from the said combining means, for deriving in response thereto a third signal which is a substantially continuous mathematical function of the first and second measurement signals, the function being such as to effect substantially complete mutual cancellation of the said additional measurement signal components, whereby the third signal comprises substantially only components corresponding to presence of the first constituent in the stream;
   second delay means, connected in the signal path of the first measurement signal between the sensing means and the secondary processing means, for establishing relative time delays between the first measurement signal as it enters the secondary processing means and the two intermediate signal versions; said second delay means introducing time delay which is partway between the time delays applied to the two intermediate signal versions respectively; and
   utilization means responding to the third signal.

2. The system of claim 1 wherein one of the pair of intermediate signal versions is delayed by a particular time interval, and the other of the pair is substantially not delayed, whereby the said relative time delay is equal to the particular time interval; and the said second delay means introduce time delay which is partway between zero and the particular time interval.

3. The system of claim 1 wherein:
   the combining means within the primary processing means combine the two intermediate signal versions in substantially equal proportions to form the arithmetic mean of the two intermediate signal versions; and
   the time delay introduced in the first measurement signal by the said second delay means being substantially halfway between the time delays respectively applied to the two intermediate signal versions.

4. The system of claim 3, wherein:
   the fluid stream is the gaseous effluent from a gas-chromatograph column;
   the said first constituent of the column's influent gas for analysis;
   the said second constituent comprises extraneous material bled from the column coating material into the flow path or extraneous material present as a constituent of the chromatograph carrier gas, or both; and
   the said monitoring station is a flow-through sample cell in a Michelson-type interferometric infrared spectrometer.

5. A system for monitoring a first constituent in a fluid stream, which stream may also include a second constituent whose concentration in the stream changes slowly relative to the changes in concentration of the first constituent, comprising:
   a monitoring station, having sensing means for deriving a first component of a first measurement signal in quantitative response to presence of such first constituent in the station;
   said sensing means also deriving an additional component of such first measurement signal in quantitative response to presence of such second constituent in the station, such additional signal component constituting a spurious signal component;
   flow means, connected to the fluid stream and the monitoring station, for directing fluid from the fluid stream through the station;
   primary signal-processing means, connected to receive the first measurement signal from the sensing means, for deriving in response to the first measurement signal a second measurement signal which has a first component and an additional component corresponding respectively to the first and additional components of the first measurement signal, the said primary signal-processing means comprising: a signal-averaging device, connected to receive the first measurement signal from the sensing means, for generating the time-average of the first measurement signal over a time interval of specified length to produce the second measurement signal, the said time interval being substantially consistent and not directly controlled by any of the signals;

secondary signal-processing means, connected to receive the first measurement signal along a signal path from the sensing means and the second measurement signal from the primary processing means, for deriving in response thereto a third signal which is substantially proportional to the difference between the first and second measurement signals, so as to effect substantially complete mutual cancellation of the said additional measurement signal components, whereby the third signal comprises substantially only components corresponding to presence of the first constituent in the stream;

time delay means, connected in the said signal path between the sensing means and the secondary signal-processing means, for causing the first measurement signal to be delayed in passing along said signal path to the secondary signal-processing means, the length of the delay being less than the said time interval over which the first measurement signal is time-averaged in the primary signal-processing means;

whereby the secondary signal-processing means in effect combine the first measurement signal with a time-average second measurement signal which is averaged over a time interval partly delayed and partly advanced relative to the effective time of the first measurement signal; and utilization means responding to the third signal.

6. The system of claim 5, wherein the length of the delay is substantially half of the said time interval;

whereby the secondary signal-processing means in effect combine the first measurement signal with a second measurement signal which is time-averaged over an interval symmetrically disposed in time relative to the effective time of the first measurement signal.

7. A system for monitoring a first constituent in a fluid stream, which stream may also include a second constituent whose concentration in the stream changes slowly relative to the changes in concentration of the first constituent, comprising:

a monitoring station, having sensing means for deriving, in quantitative response to presence of such constituents in the station, a first measurement signal which is the resultant of a first signal component due to said first constituent and an additional signal component due to said second constituent, the signal component due to the first constituent being desired and that due to the second constituent being spurious;

flow means, connected to the fluid stream and the monitoring station, for directing fluid from the fluid stream through the station;

primary signal-processing means, connected to receive the first measurement signal from the sensing means, for deriving in response to the first measurement signal a second measurement signal which is a time-distorted version of the first measurement signal and which has a first component and an additional component corresponding respectively to the first and additional components of the first measurement signal;

the primary signal-processing means introducing into the second measurement signal a time-distortion which is a substantially consistently applied function of time; said function being not directly controlled by any of the signals, and said function having associated with it a characteristic time interval;

signal-delay means, connected to receive the first measurement signal from the sensing means, for deriving in response to the first measurement signal a third measurement signal which is a delayed version of the first measurement signal and which has a first component and an additional component corresponding respectively to the first and additional components of the first measurement signal;

the signal-delay means introducing into the third measurement signal a time delay which is partway between zero and the said characteristic time interval;

secondary signal-processing means, connected to receive the second measurement signal along a signal path from the primary signal-processing means and the third measurement signal along a signal path from the signal-delay means, for deriving in response thereto a fourth signal which is a substantially continuous mathematical function of the second and third measurement signals, the function being such as to effect substantially complete mutual cancellation of the said additional measurement signal components, whereby the fourth signal comprises substantially only components corresponding to presence of the first constituent in the stream; and utilization means responding to the fourth signal.

8. The system of claim 7 wherein the primary signal-processing means comprise:

signal-splitting means, connected to receive the first measurement signal from the sensing means, for generating a pair of intermediate signal versions in response to the first measurement signal, each having substantially the same sequence of amplitudes and frequencies as the first measurement signal;

further delay means, connected to receive one of the two intermediate signal versions from the signal-splitting means, for delaying that one of the intermediate signal versions by the said characteristic time interval, said characteristic interval being substantially consistent and not directly controlled by any of the signals; and combining means, connected to receive one of the two intermediate signal versions from the signal-splitting means and connected to receive the other intermediate signal version after delay from the said further delay means, for generating the said second measurement signal by additive recombination of the two intermediate signal versions in specified proportions;

said generating of a pair of signals, delay and additive recombination constituting said time-distortion; the said combining means also being connected to transmit the said second measurement signal to the secondary processing means.

9. The system of claim 8 wherein the said signal-delay means introduce a delay interval which is approximately half of the said characteristic time interval.

10. The system of claim 7 wherein the primary signal-processing means comprise:
 a signal-averaging device, connected to receive the first measurement signal from the sensing means, for generating the time-average of the first measurement signal over an averaging time interval equal to the characteristic time interval;
 said generating of a time-average of the first measurement signal constituting said time-distortion; said signal-averaging device also being connected to transmit the said second measurement signal to the secondary processing means.

11. The system of claim 10 wherein the said signal-delay means introduce a time delay which is approximately half the said characteristic time interval.

12. A system for monitoring a first constituent in a fluid stream, which stream may also include a second constituent whose concentration in the stream changes slowly relative to the changes in concentration of the first constituent, comprising:
 a monitoring station, having sensing means for deriving, in quantitative response to presence of such constituents in the station, a first measurement signal which is the resultant of a first signal component due to said first constituent and an additional signal component due to said second constituent, the signal component due to the first constituent being desired and that due to the second constituent being spurious;
 flow means, connected to the fluid stream and the monitoring station; for directing fluid from the fluid stream through the station;
 primary signal-processing means, connected to receive the first measurement signal from the sensing means, for deriving at each moment during system operation a second measurement signal by additive combination of a plurality of samples of the first measurement signal taken at a plurality of moments during a time interval; whereby the second measurement signal has a first component and an additional component corresponding respectively to the first and additional components of the first measurement signal;
 each of the two endpoints of said time interval being one of said plurality of moments; and the distribution in time of said plurality of moments at which said samples are taken bearing a substantially consistent relationship to the corresponding moment at which the corresponding second measurement signal is derived, said relationship being not directly controlled by any of the signals;
 signal-delay means, connected to receive the first measurement signal from the sensing means, for deriving in response thereto a third measurement signal by sampling the first measurement signal at a moment which is partway between the said endpoints; whereby the third measurement signal has a first component and an additional component corresponding respectively to the first and additional components of the first measurement signal;
 secondary signal-processing means, connected to receive the second measurement signal along a signal path from the primary signal-processing means and the third measurement signal along a signal path from the signal-delay means, for deriving in response thereto a fourth signal which is a substantially continuous mathematical function of the second and third measurement signals, the function being such as to effect substantially complete mutual cancellation of the said additional measurement signal components, whereby the fourth signal comprises substantially only components corresponding to presence of the first constituent in the stream; and
 utilization means responding to the fourth signal.

13. The system of claim 12 wherein the signal-delay means form the third measurement signal by sampling the first measurement signal at a moment which is approximately at the center of said time interval.

* * * * *